United States Patent
Kavalkovich et al.

(10) Patent No.: US 6,761,887 B1
(45) Date of Patent: Jul. 13, 2004

(54) ALGINATE LAYER SYSTEM FOR CHONDROGENIC DIFFERENTIATION OF HUMAN MESENCHYMAL STEM CELLS

(75) Inventors: Karl Kavalkovich, Baltimore, MD (US); Raymond Boynton, Watertown, MA (US); Mary Murphy, Baltimore, MD (US); Frank Barry, Baltimore, MD (US)

(73) Assignee: Osiris Therapeutics, Inc., Baltimore, MD (US)

( * ) Notice: Subject to any disclaimer, the term of this patent is extended or adjusted under 35 U.S.C. 154(b) by 0 days.

(21) Appl. No.: 09/831,424

(22) PCT Filed: Nov. 16, 1999

(86) PCT No.: PCT/US99/27129

§ 371 (c)(1),
(2), (4) Date: Jun. 21, 2001

(87) PCT Pub. No.: WO00/29552

PCT Pub. Date: May 25, 2000

Related U.S. Application Data

(60) Provisional application No. 60/108,594, filed on Nov. 16, 1998.

(51) Int. Cl.[7] .......................... C12N 11/10; C12N 11/04; C12N 5/06; C12N 5/08
(52) U.S. Cl. ...................... 424/93.7; 424/426; 435/178; 435/182; 435/395
(58) Field of Search ................................ 435/178, 182, 435/325, 395; 424/93.7, 426

(56) References Cited

FOREIGN PATENT DOCUMENTS

| WO | WO 96/28539 | * | 9/1994 |
| WO | WO 98/25653 | * | 6/1998 |
| WO | WO 98/32333 | * | 7/1998 |

* cited by examiner

Primary Examiner—David M. Naff
(74) Attorney, Agent, or Firm—Elliot M. Olstein; Raymond J. Lillie

(57) ABSTRACT

Disclosed are a composition of chemically defined components which support in vitro and in vivo chondrogenesis of mesenchymal stem cells, a method for in vitro and in vivo chondrogenic induction of such stem cells, and a method of forming human chondrocytes in vitro and in vivo from such stem cells.

16 Claims, 9 Drawing Sheets

Alginate Layer MSC Chondrogenesis Histology

Day 14

CROSS SECTION VIEW OF LAYER 2.5-1mm thick

FIG. 4A
FIG. 4B
(A) Alginate Cultures
(B) Pellet Cultures
Day 0
Day 7
Day 14
Day 21
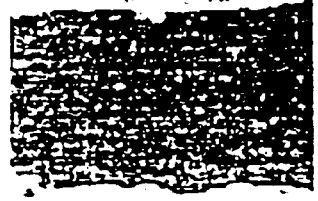
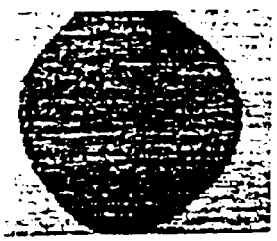
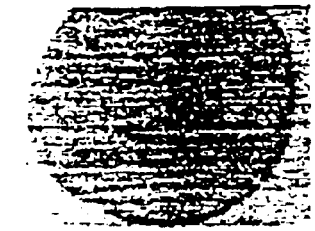
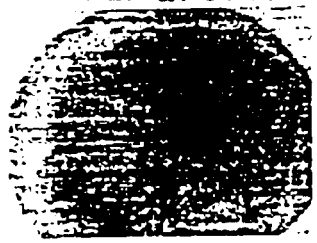

F I G. 7
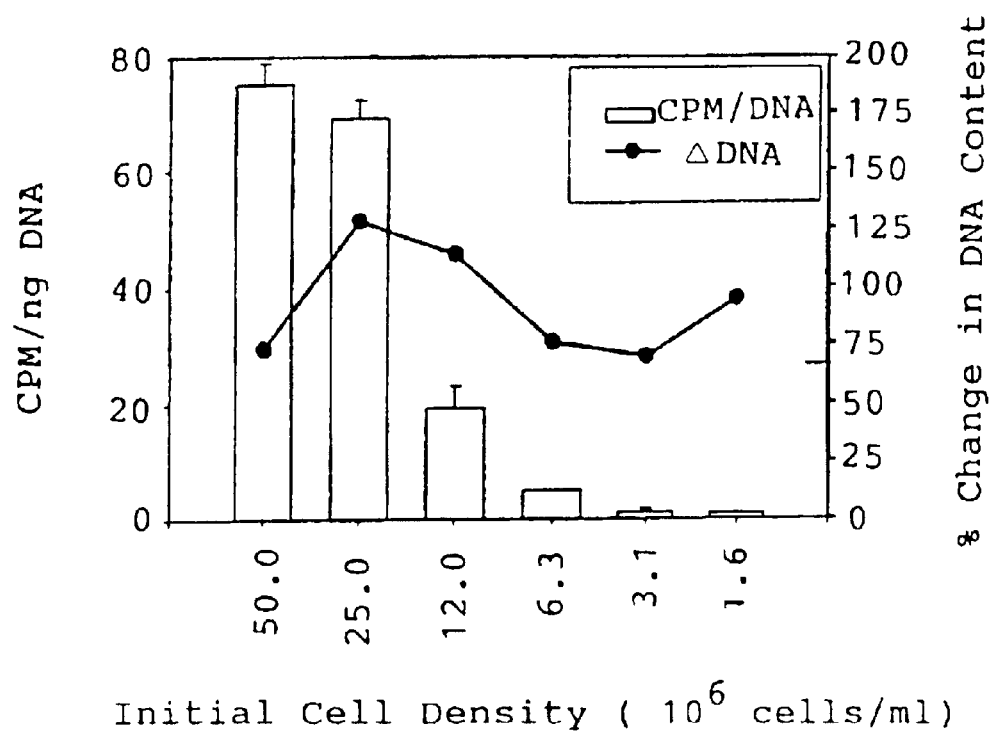

ALGINATE LAYER SYSTEM FOR CHONDROGENIC DIFFERENTIATION OF HUMAN MESENCHYMAL STEM CELLS

This application claims priority based on provisional application Serial No. 60/108,594, filed Nov. 16. 1998.

The present invention relates to the field of methods and compositions for directing human mesenchymal stem cells in vitro and in vivo to differentiate into chondrocytes prior to or at the time of, or after their implantation into a recipient or host for the therapeutic treatment of articular cartilage defects.

Mesenchymal stem cells (MSCs) are the formative pluripotent blast or embryonic-like cells found in bone marrow, blood, dermis, and periosteum that are capable of differentiating into specific types of mesenchymal or connective tissues including adipose, osseous, cartilaginous, elastic, muscular, and fibrous connective tissues. The specific differentiation pathway which these cells enter depends upon various influences such as mechanical influences and/or endogenous bioactive factors, including growth factors cytokines and/or local microenvironmental conditions established by host tissues.

A clonal rat fetus calvarial cell line has been shown to differentiate into muscle, fat, cartilage and bone (Goshima et al., Clin Orthop Rel Res. 269:274–283, 1991). Bone marrow cells form bone and cartilage following their encasement in diffusion chambers and in vivo transplantation (Ashton et al., Clin Orthop Rel Res. 151:294–307, 1980 (rabbit): Bruder et al., Bone Mineral. 11:141–151, 1990 (avian)). Cultured chick periosteum cells have been shown to differentiate into cartilage and bone in vitro (Nakahara et al., Exp. Cell Res., 195:492–503; 1991). Rat bone marrow-derived mesenchymal cells were shown to have the capacity to differentiate into osteoblasts and chondrocytes when implanted in vivo (Dennis et al., Cell Transpl, 1:2332, 1991; Goshima et al., Clin Orthop Rel Res. 269:274–283, 1991).

Chondrogenic differentiation of rabbit bone marrow derived mesenchymal progenitor cells has been studied in connection with articular cartilage healing utilizing cells in a pelleted format (Johnstone et al. Exp Cell Res 238(1) :265–272 (1998).). However, cells in a condensed packed or pelleted cell mass do not have an optimal configuration in part due to the limitation on the maximum growth of the cells, limited permeability of nutrients, gases and growth factors, and other metabolic characteristics.

Pre-molded biodegradable multilayer matrices have been described for repair of articular cartilage, which have been packed into or press-fitted into regularly shaped osteochondral defects (Athanasiou U.S. Pat. No. 5,607,474). Cultured chondrocytes added to a collagen matrix for implantation into an articular cartilage lesion have also been described (Frenkel, S R et al., J Bone Joint Surg, 79-B(5):831–6 (1997)).

Alginate sponges have been used in studies of cartilage repair (see review Messner K. and J. Gilquist, Acta Orthop. Scand 67(5):523–529 (1996)). Mesenchymal cells from 12 day old mouse limb buds that were phenotypically undifferentiated but committed to differentiate to the chondrocytic lineage in an alginate bead culture system differentiated to cartilage cells and formed a pericellular matrix (Shakibaci, M. and P. De Souza, Cell Biology International. 21(2):75–86 (1997)). Adult human chondrocytes cultured in alginate beads formed a compartmentalized cartilage matrix (Häuselmann H J et al., Am. J. Physiol. 271 (Cell Physiol. 40):C742–C752, 1996). The growth of chondrocytes in alginate and collagen carrier gels has been compared (van Susante, J. et al., Acta Orthop Scand. 66(6):549–556 (1995)).

An optimized matrix to regenerate cartilage in vivo using mesenchymal stem cells is therefor required.

SUMMARY OF THE INVENTION

In accordance with one aspect of the invention, there is provided a construct which supports the differentiation and maturation of human mesenchymal stem cells into chondrocytes. In a preferred embodiment, the construct comprises human mesenchymal stem cells in association with a gel and preferably in an alginate suspension. The construct can be utilized for in vivo cartilage regeneration.

In a further aspect of the invention, soluble hyaluronic acid may be added to the construct to support chondrogenesis.

In accordance with another aspect, there is provided a composition for regenerating cartilage comprising human mesenchymal stem cells and an alginate gel. Preferably the matrix supports the differentiation and maturation of human mesenchymal stem cells into chondrocytes.

In one embodiment, the construct can be placed in vitro in culture media which will provide conditions favorable for chondrogenic differentiation of the MSCs in the gel. The constructs are cultured in this media and may be modified to determine the effect of specific agents on chondrogenic differentiation and/or the chondrocytic phenotype.

In another embodiment, the MSCs are added to the gel in vitro under conditions such that the MSCs attach to the gel to form an MSC-gel construct. The construct can then be placed in vivo, i.e. implanted at a target site. In this embodiment, the MSCs are not induced to differentiate into chondrocytes prior to implantation. When placed in vivo, the construct will be exposed to naturally occurring chondrogenic inducing factors, found for example in synovial fluid, to stimulate chondrogenic differentiation of the MSCs.

In a still further embodiment, the MSCs are added to the alginate solution and the MSC-alginate solution is placed in contact with chondrogenic medium in vitro for a period of time sufficient to direct the MSCs into the chondrogenic lineage. The culture period may be long enough to obtain either mature chondrocytes or may be interrupted at any stage of the chondrogenic differentiation. The entire construct or portions thereof may then be implanted into the defect site.

In another aspect of this embodiment, the MSCs are added to the alginate solution and the MSC alginate suspension is spread on a support. The alginate suspension is contacted with a $CaCl_2$ solution. The alginate polymerizes and forms a gel layer encasing the MSCs. The layer may then be contacted with a chondrogenesis inducing factor.

For purposes of the present invention, the MSCs can be culture-expanded MSCs, freshly isolated MSCs or unpurified populations of MSCs. The MSCs may further be exposed to at least one chondroinductive agent.

Hyaluronic acid may be further added to the above embodiments to support chondrogenesis.

The invention also provides a process for producing chondrocytes from mesenchymal stem cells by contacting mesenchymal stem cells with a chondroinductive agent in vitro wherein the stem cells are associated with the alginate gel and then placed into the implant site.

The invention also provides a process for inducing chondrogenesis in mesenchymal stem cells by contacting mesenchymal stem cells with a chondroinductive agent in vitro wherein the stem cells are associated with an alginate gel. The culture period may be long enough to obtain either mature chondrocytes or may be interrupted at any stage of the chondrogenic differentiation. The entire construct or portion of the construct may be delivered to the defect site.

The invention further provides a method of repairing or regenerating damaged cartilage, comprising administering to an individual in need thereof a biocompatible construct comprising an alginate gel which supports the differentiation of human mesenchymal stem cells into the chondrogenic lineage.

The above methods can also preferably comprise steps where the cells are cultured with the chondroinductive composition and thereafter mixed in alginate gel suspension.

The above methods can further comprise steps where the cells are cultured with soluble hyaluronic acid and thereafter are mixed in alginate gel suspension.

In another embodiment of the present invention, the MSC-gel layer system may be delivered directly to the implant site without prior induction of differentiation of the MSCs to the chondrogenic lineage. In this embodiment the MSCs are allowed to attach to the gel for a period of up to 24 hours and then implanted without attempting to direct them into the chondrogenic lineage prior to implantation.

In an alternate embodiment, the MSC-loaded gel is placed into chondrogenic medium in vitro for a finite period to direct the MSCs into the chondrogenic lineage. The culture period may be long enough to obtain mature chondrocytes or may be interrupted at any stage of the chondrogenic differentiation. The entire construct or portions thereof may be delivered to the defect site.

BRIEF DESCRIPTION OF THE DRAWINGS

FIG. 7. Rate of $^{35}$S-sulfate incorporation in MSCs plated at different initial cell densities.

DETAILED DESCRIPTION OF THE INVENTION

Figure 1:
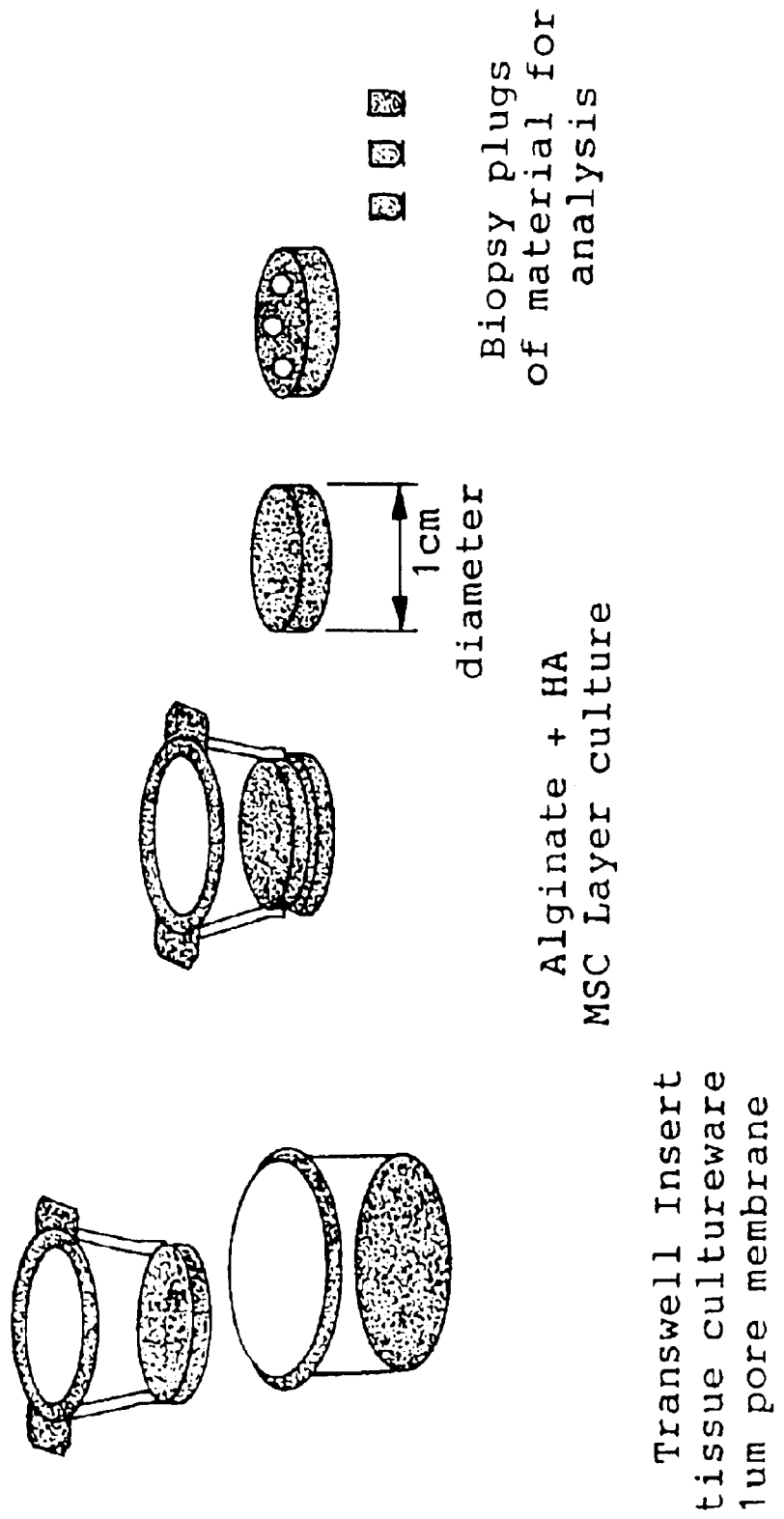
FIG. 1 illustrates an MSC-alginate-HA suspension layered onto the membrane surface of a transwell insert tissue culture well.

The present invention provides a composition for the repair of cartilage defects by the rapid regeneration of cartilage tissue. The composition is, for example, inserted or implanted into the defect resulting in articular cartilage regeneration and repair of the defect.

The composition comprises an alginate layer in combination with isolated mesenchymal stem cells. The alginate can be combined with the cartilage regenerative cells and optionally other active ingredients by forming a suspension of the MSCs and the alginate where the suspension liquid can have other active ingredients dissolved.

Alginate is an unbranched linear polysaccharide consisting of $\beta$-D mannuronic acid and $\alpha$-L guluronic acid. It polymerizes and forms a gel in the presence of divalent cations such as $Ca^{++}$.

In one embodiment, the composition can contain additional components such as chondroinductive factors. The cells and/or the alginate gel can be contacted with a chondroinductive factor. As used herein the terms "chondroinductive agent" or "chondroinductive factor" refers to any natural or synthetic, organic or inorganic chemical or biochemical compound or combination or mixture of compounds, or any mechanical or other physical device, container, influence or force that can be applied to human mesenchymal stem cells which are in a three dimensional format so as to effect their in vitro chondrogenic induction or the production of chondrocytes. The chondroinductive agent is preferably selected, individually or in combination, from the group consisting of (i) a glucocorticoid, such as dexamethasone, and (ii) a member of the transforming growth factor superfamily, such as a bone morphogenic protein (preferably BMP-2 or BMP-4). TGF-$\beta$, inhibin A or chondrogenic stimulating activity factor (CSA).

The invention also provides a method for treating a cartilage detect in an animal, particularly a mammal, and more particularly a human in need thereof, which comprises administering to the cartilage defect of said animal a cartilage-regenerative amount of the composition of the invention.

In one embodiment, the cells are contacted with a chondroinductive factor while in the alginate gel layer ex vivo. Thus the method can further comprise administering at least one chondroinductive factor which further induces or accelerates the differentiation of such mesenchymal stein cells into the chondrogenic lineage.

In another embodiment, the MSCs are first combined with the alginate suspension and polymerized within the gel and are then implanted without induction to chondrogenesis. In a still further embodiment. MSCs are loaded into the alginate and then placed in chondrogenesis-inducing media to induce differentiation prior to delivery to the defect site.

This invention has multiple uses and advantages. One such advantage lies in the ability to direct and accelerate MSC differentiation prior to implantation into the host. For example, MSCs which are directed in vitro to become chondrogenic cells will synthesize cartilage matrix at an implant site more rapidly and uniformly than MSCs which must first be recruited into the lineage and then progress through the key differentiation steps. Such an ex vivo treatment also provides for uniform and controlled application of bioactive factors to purified MSCs, leading to uniform lineage commitment and differentiation. In addition, by pretreating the MSCs prior to implantation, potentially harmful side effects associated with systemic or local administration of exogenous bioactive factors are avoided. Another use of this technique lies in the ability to direct tissue regeneration based on the stage of differentiation of the cells at the time of implantation, which, with respect to cartilage, may control the ultimate tissue type formed.

The cells are grown and maintained in a growth or culture medium in which the composition of the invention can undergo in vitro chondrogenesis, particularly in accordance with the methods of the invention, such as serum-free animal cell culture preparation or medium of known composition which will support the viability of human mesenchymal stem cells in vitro.

The human mesenchymal stem cells utilized for purposes of the present invention can be derived, for example, from bone marrow. Although these cells are normally present at very low frequencies in bone marrow, a process for isolating, and culture expanding the population of these cells in tissue culture is reported in Caplan et al. U.S. Pat. No. 5,486,359.

In one embodiment, the mesenchymal stem cells are preferably isolated, culture expanded human mesenchymal stem cells in a chemically defined serum-free medium which comprises (1) a chemically defined minimum essential medium (e.g., any of the Eagle's based media, i.e., Dulbecco's Modified Eagle's Medium (DMEM); Iscove's Modified Eagle's Medium, alpha Modified Eagle's Medium, and also McCoy's 5A and BGJb (Fitton-Jackson Modification)); (2) ascorbate or an analog thereof; (3) an iron source; (4) insulin or an insulin-like growth factor; and (5) at least one chondroinductive agent or factor.

It is also possible to use an isolated, non-cultured human mesenchymal stem cell preparation in the composition and methods of the invention. MSCs can be isolated as a non-cultured preparation, such as by density gradient fractionation, from tissue such as bone marrow, blood (including peripheral blood), periosteum and dermis, and other tissues which have mesodermal origins, so as to be substantially free of other types of cells in the marrow. A monoclonal antibody separation is then performed as follows. Dynabeads M-450 (Dynal Inc., Lake Success, N.Y.) are coupled to anti-MSC monoclonal antibodies having ATCC Accession Numbers HB 10743, HB 10744 and HB 10745, by incubating antibody with secondary antibody coated Dynabeads (2.0 g anti-MSC antibody/mg Dynabead; $1 \times 10^7$ Dynabeads/ml) in PBS for 30 minutes at 4° C.

The cells are suspended in a solution of sodium alginate and the suspension is distributed on a semiporous membrane as a layer, the shape and dimensions of which can be easily modified. The alginate mixture is solidified by immersion of the layer and supporting membrane in a pool of calcium chloride.

In a preferred embodiment the alginate layer system comprises a component that provides for two separate media-tissue interfaces. This has the advantage of simulating the division of nutritional support seen in vivo between the subchondral vascular supply and the synovial fluid proximal to the articular surface. Nutritional or signalling gradients may be established by manipulating the media to formulations in either media compartment.

Simple disks of material may be cast and cultured for use as an in vitro testing platform permitting easier sample manipulations and multiple analysis from the same sample. Biochemical, molecular and biomechanical analysis is possible from the same sample. The system is ideally suited for studying the effects of bioactive substances involved in modulating the differentiation of MSCs and represents a format for high throughput screening of substances involved in the turnover of the extracellular matrix molecules in cartilage under normal and osteoarthrtic conditions.

The cell density within the construct can easily be varied. Construct shape is defined by the dimensions and conformation of the supporting membrane and may be further modified by progressive layering and solidifying of the alginate mixture. Layering in this fashion could also be used to modify cellularity as a function of depth. Thicknesses approaching articular cartilage (0.5–4.0 mm) are achievable. This leads to possible uses as an implantable tissue construct for surgical applications. In this aspect, MSCs are culture expanded to appropriate numbers, cast in an alginate layer, sized and shaped to fit an individual's cartilage defect (or larger). The construct is cultured under conditions which are conducive to chondrogenic differentiation. The newly formed chondrocytes express and organize extracellular matrix molecules into a tissue which is comparable to articular cartilage in its responsiveness to physiological and biomechanical stresses. Within a matter of days of ex vivo culture, this tissue is surgically implanted or grafted into the site of the defect.

Whereas particular embodiments of the invention are described herein for purposes of illustration, it will be evident to those skilled in the art that numerous variations of the details may be made without departing from the invention as defined in the appended claims.

EXAMPLE 1

Figure 2:
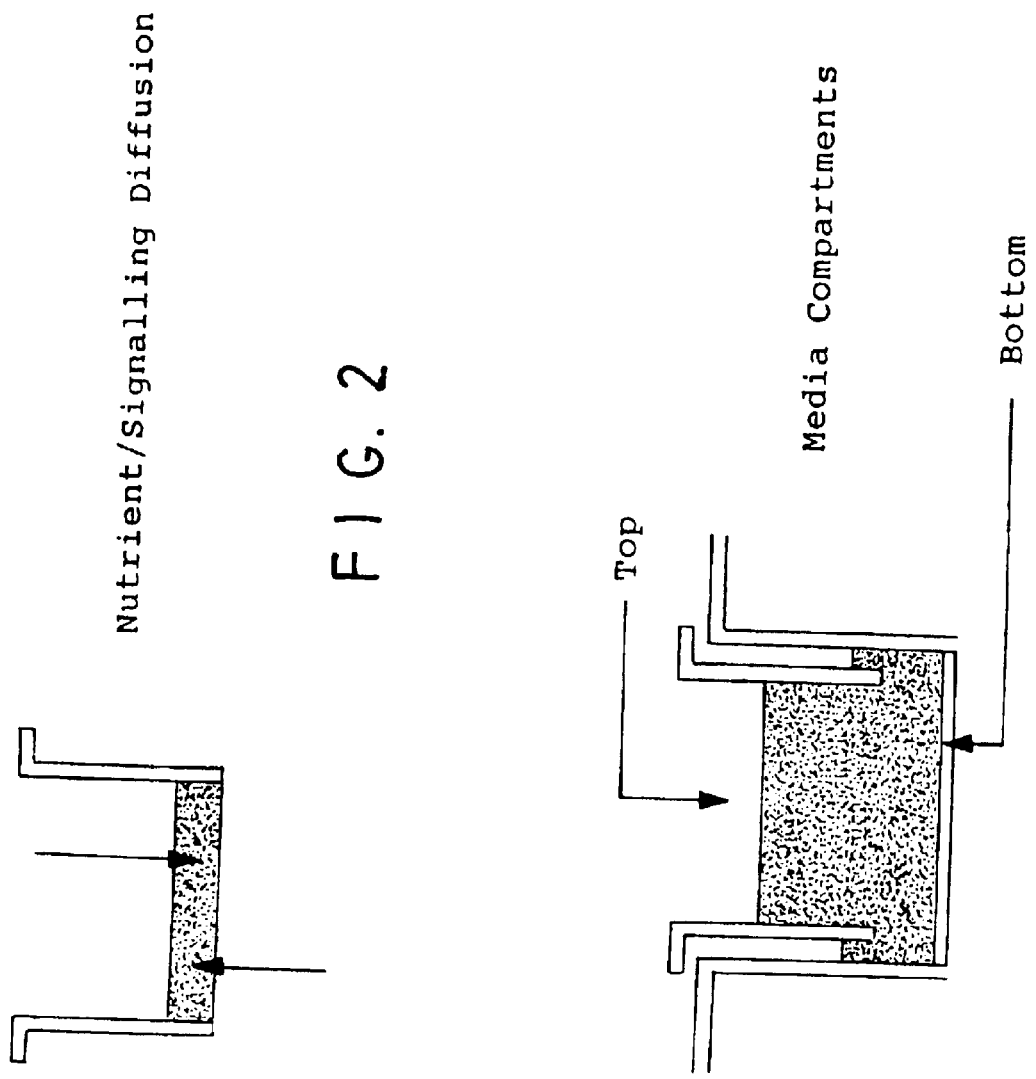
FIG. 2 illustrates the layer system of MSC-alginate-HA coated transwell in a tissue culture well with complete chondrogenic media and chondrogenesis inducing factor above and incomplete chondrogenic media below the transmembrane layer.

Mesenchymal stein cell were obtained from human bone marrows (Poetic Technologies. Gaithersburg. Md.). Following normal expansion culture, $4 \times 10^6$ hMSCs were spun down and washed with 0.5 M NaCl. The cells were resuspended in 10 μl sodium alginate (Monsanto, San Diego, Calif.) (2.4% (v/v) in 0.15 M NaCl, sterilized using a 0.45 μm filter) and 10 μl soluble HA (HEALON (Pharmacia, Piseataway, N.J.) 2 μg/ml in sterile MQ $H_2O$). This cell suspension was spread onto the membrane surface of a FALCON® transwell-insert tissue culture well (Becton-Dickinson, N.J.) (see FIG. 1). The transwell membrane (1.0 μm pore size) serves as a support for the layer while the alginate polymerizes and forms a gel when the transwell is immersed in sterile 100 mM $CaCl_2$ for 10 minutes. Following solidification of the layer, the $CaCl_2$ as removed and the layer with transwell was washed in 0.15M NaCl three times and twice with complete chondrogenic media (Table 1) containing 10 ng/ml recombinant human TGF-β3 (Oncogene Sciences. Cambridge. Mass.) was added above the layer, incomplete chondrogenic media (Table 2) below (see FIG. 2). Culture of the layer proceeded for 14 days feeding twice per day due to the high cell density. At the end of this period the tissue was fixed for histological evaluation.

Figure 3:
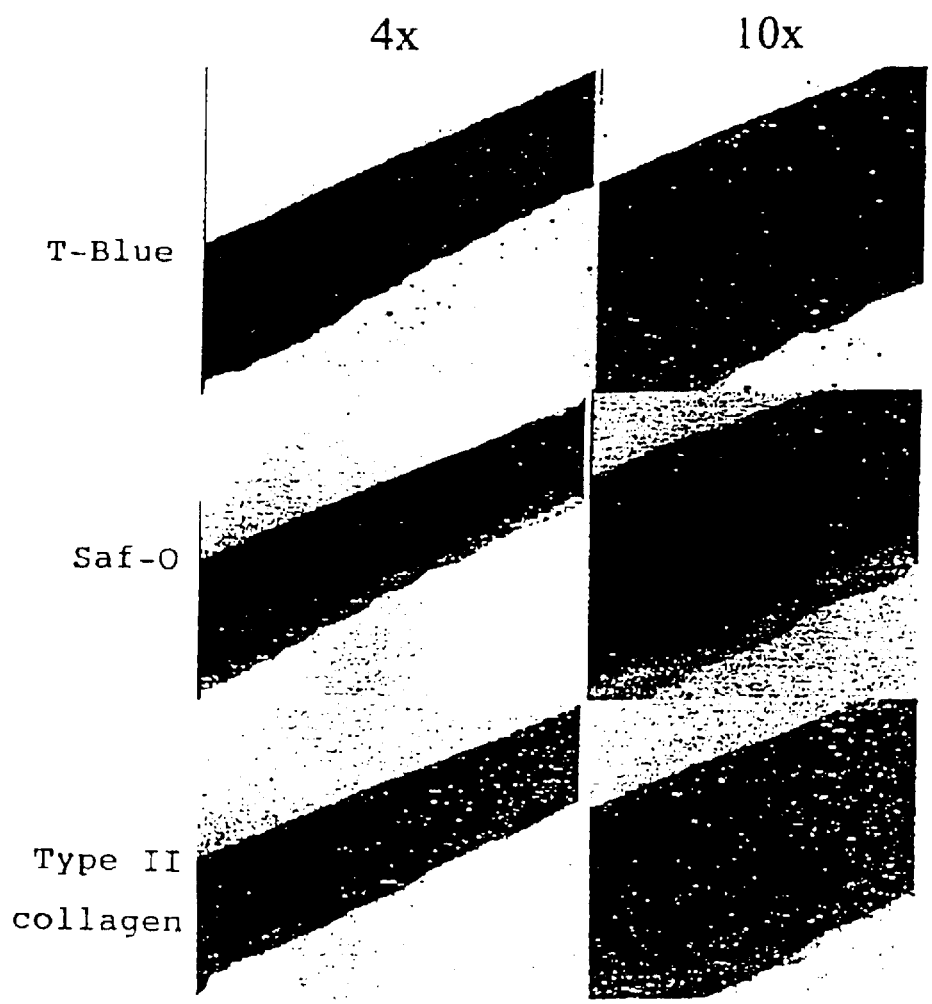
FIG. 3 shows a cross section view of the alginate-MSC layer after 14 days in culture after histological staining with toluidine-blue, safrinin-O and immunohistochemical staining of collagen Type II tissue.

Histological staining revealed positive markers of chondrogenesis in >90% of the tissue. Uniform staining by toluidine blue and safranin-O indicated sulfated proteoglycan production. Likewise, evenly distributed immunohistochemical staining of collagen type II indicated a cartilage-like tissue (see FIG. 3).

TABLE 1

Complete Chondrogenic Medium

| Ingredient | Stock | Dilution | Final Concentration |
|---|---|---|---|
| DMEM (high glucose) | as supplied | n/a | Undiluted |
| ITS + supplement | as supplied | 1:99 | 6.25 μg/ml bovine insulin 6.25 μg/ml transferrin 6.25 μg/ml selenous acid 5.33 μg/ml linoleic acid 1.25 mg/ml BSA |
| Dexamethasone[1] | 1 mM in EtOH | 2 serial | 100 nM |

TABLE 1-continued

Complete Chondrogenic Medium

| Ingredient | Stock | Dilution | Final Concentration |
|---|---|---|---|
| | (FW = 392) | 1:99 each | |
| Ascorbic acid-2-phosphate (AA2P)[2] | 5 mg/ml (FW = 290) | 1:99 | 50 µg/ml |
| Proline[2] | 4 mg/ml (FW = 115) | 1:99 | 40 µg/ml |
| Sodium pyruvate | 100 mM | 1:99 | 1 mM |
| Antibiotic-antimycotic | as supplied | 1:99 | 100 U/ml penicillin 100 µg/ml streptomycin 250 ng/ml amphotericin B |
| TGF-β3[3] | 5 µg/ml | 1:500 | 10 ng/ml |

[1]Dexamethasone powder is dissolved in absolute ethanol (3.92 mg per 10 ml), filter sterilized and stored at 4° C.
[2]Stocks of AA2P and proline are made by dissolving powder into DMEM and filter-sterilizing. Aliquots of these stocks may be frozen at −20° C. and stored for two weeks.
[3]TGF-β3 stock is made by resuspending lyophilized powder in sterile liquid using siliconized pipet tips and 0.5 ml tubes. 1 µg of TGF-β3 is resuspended in 50 µl of 10% ethanol/10 mM HCl, then divided into aliquots and stored at −80° C. for up to 2 months.

TABLE 2

Incomplete Chondrogenic Medium

| Ingredient | Stock | Dilution | Final Concentration |
|---|---|---|---|
| DMEM (high glucose) | as supplied | n/a | Undiluted |
| ITS + supplement | as supplied | 1:99 | 6.25 µg/ml bovine insulin 6.25 µg/ml transferrin 6.25 µg/ml selenous acid 5.33 µg/ml linoleic acid 1.25 mg/ml BSA |
| Dexamethasone[1] | 1 mM in EtOH (FW = 392) | 2 serial 1:99 each | 100 nM |
| Ascorbic acid-2-phosphate (AA2P)[2] | 5 mg/ml (FW = 290) | 1:99 | 50 µg/ml |
| Proline[2] | 4 mg/ml (FW = 115) | 1:99 | 40 µg/ml |
| Sodium pyruvate | 100 mM | 1:99 | 1 mM |
| Antibiotic-antimycotic | as supplied | 1:99 | 100 U/ml penicillin 100 µg/ml streptomycin 250 ng/ml amphotericin B |

[1]Dexamethasone powder is dissolved in absolute ethanol (3.92 mg per 10 ml), filter sterilized and stored at 4° C.
[2]Stocks of AA2P and proline are made by dissolving powder into DMEM and filter-sterilizing. Aliquots of these stocks may be frozen at −20° C. and stored for two weeks.

EXAMPLE 2

Comparison of Chondrogenic Cultures of MSCs in Alginate Layers and in Pellets

MSCs were isolated from human bone marrow and cultured under chondrogenic conditions in pellet format and in alginate layers. Samples were harvested for immunocytochemical detection of collagen Type II at 7, 14 and 21 days. The cells were seeded on the alginate at a density of $25 \times 10^6$ cells/ml of alginate gel. Pellets were prepared using $2 \times 10^5$ cells/pellet. Within the alginate cultures deposition of collagen Type II was evident at day 7 (FIG. 4A) and was distributed uniformily throughout the inter-territorial matrix by day 14. After 21 days, the layer noticeably as thicker with a dense extracellular matrix and the cells were similar morphologically to chondrocytes. These alginate layer cultures were compared with pellet cultures of MSCs taken from the same donor and grown under the same nutrient conditions. Immunocytochemical analysis of the pellet cultures (FIG. 4B) indicated that the deposition of collagen Type II occurred substantially later in the pellets compared to the alginate culture. This is demonstrated clearly by comparing the level of collagen Type II staining in both cultures at 14 days (FIGS. 4A and 4B). Furthermore, the cellular morphology was more uniform in the alginate cultures compared to the pellets. After 21 days under chondrogenic conditions, the cells in the alginate layer had a homogeneous appearance with uniform staining while the pellets had heterogeneous staining and cells of variable morphology. In particular, the outer periphery of the pellet had cells which were flattened and did not express collagen Type II, an observation that has been made previously. In the alginate layer it appeared that all the cells, including those in the superficial zones, were differentiated, showing both chondrocytic morphology and collagen Type II staining.

Figure 4C:
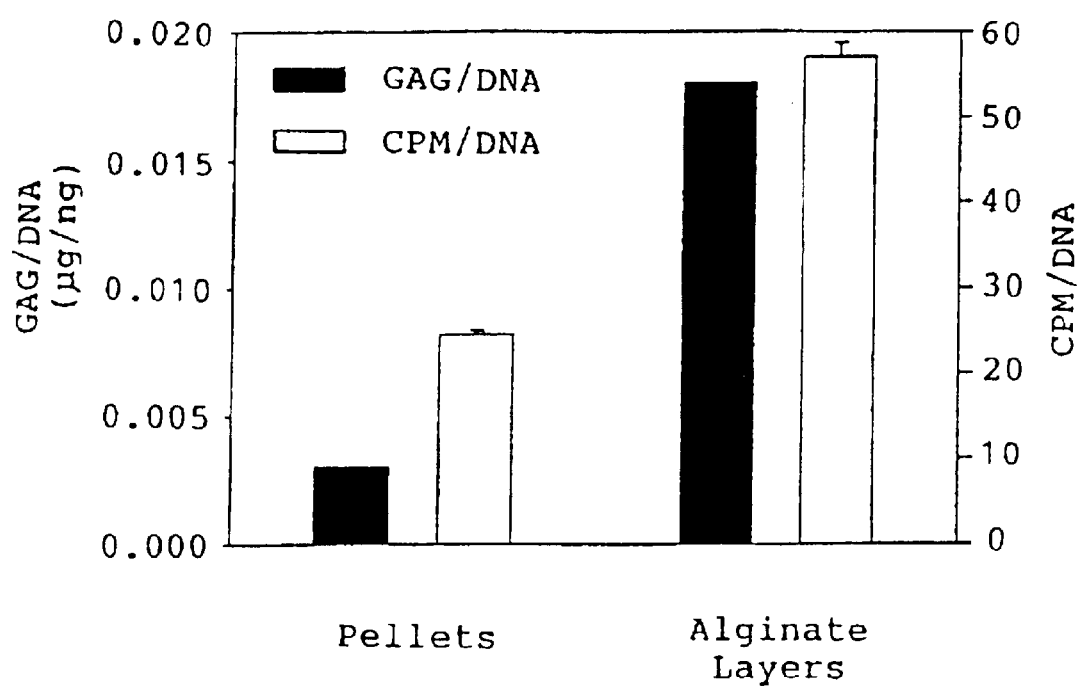
FIG. 4. MSCs cultured under chondrogenic conditions in (A) alginate layer and (B) pellets for up to 21 days and then stained for reactivity with a collagen Type II-specific antibody, (C) Accumulated GAG and rate of biosynthesis measured after 14 days for both alginate and pellet cultures.

Analysis of the accumulation of sulfated glycosaminoglycans (GAG) was carried out by measuring the amount of dimethylmethylene blue-reactive material in extracts of both alginate layers and pellets (FIG. 4C). The rate of GAG synthesis was determined by measuring the incorporation of $^{35}$S-sulfate at 14 days. Both measurements are given per ng DNA, indicating the level of activity per cell. The amount of accumulated GAG was approximately 6-fold higher in the alginate culture compared to the pellet and the rate of GAG synthesis was about 2.5-fold higher. Incorporated $^{35}$S-sulfate released into the culture media comprised approximately 10% and 4%, respectively, of the total GAG synthesized in pellet cultures and in alginate layers.

EXAMPLE 3

Effect of Addition of Hyaluronan (HA)

Figure 5:
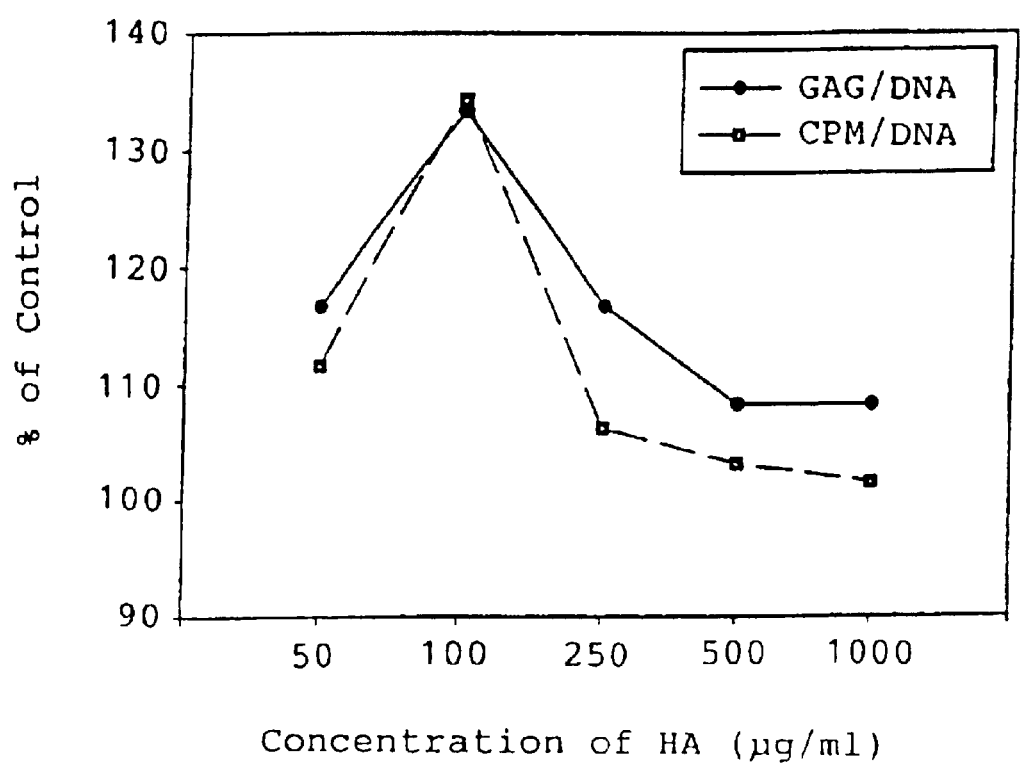
FIG. 5. Accumulation of GAG and rate of biosynthesis measured as a function of concentration of added HA. The HA concentration ranted from 50 to 1,000 $\mu$g/ml. Measurements were taken after 14 days in culture.
Figure 6A:
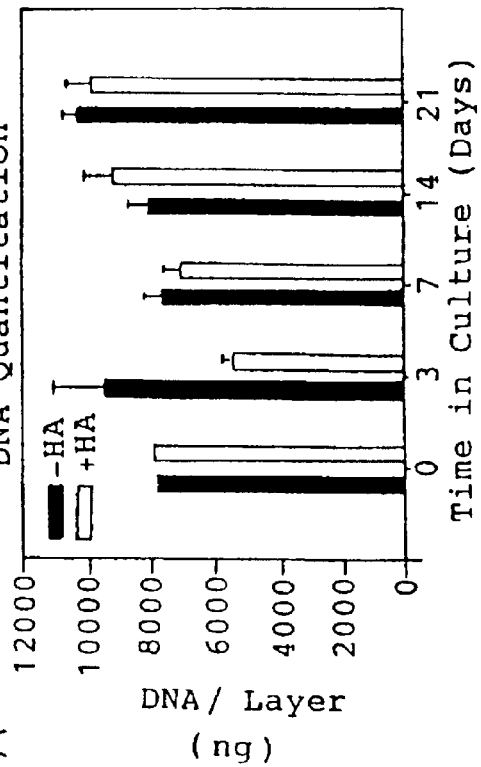
FIG. 6. Accumulation of GAG, DNA content, and rate of $^{35}$S-sulfate incorporation in MSCs to which hyaluronan was or was not added.
Figure 6B:
Figure 6C:
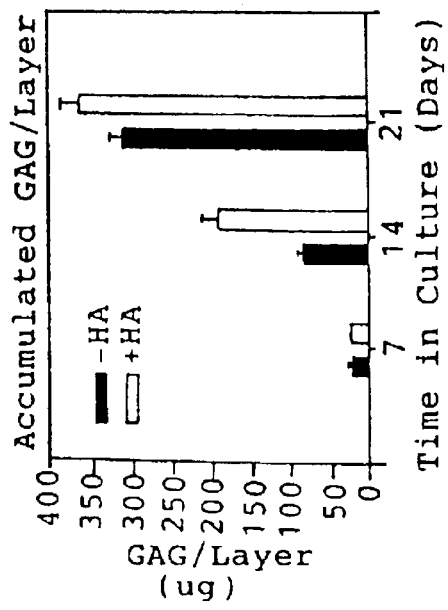
Figure 6D:
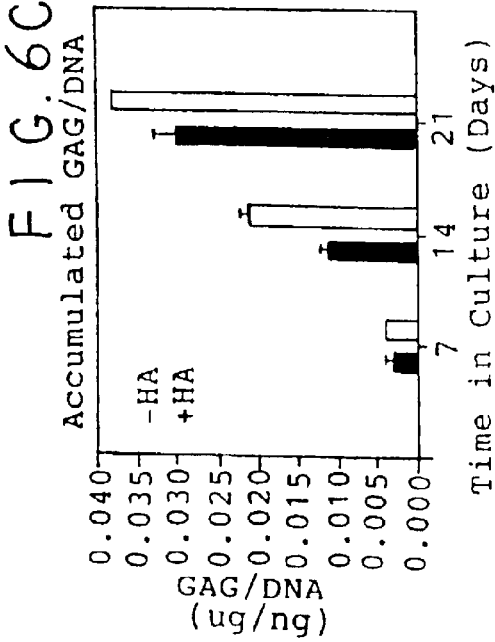

The effect of adding high molecular weight HA during the initial alginate layer formation was tested over a range of concentrations from 50–1000 µg/ml (FIG. 5). GAG accumulation and synthesis at day 14 both were measured over the range of HA concentrations studied. Under these conditions, the effect of added HA was greatest at 100 µg/ml HA.

To evaluate in more detail the manner in which HA influenced matrix deposition, cultures were maintained over a longer time period with and without added HA. Cells were mixed with 250 µg/ml of HA at a seeding density of $25 \times 10^6$ cells/ml. Samples were harvested at 7, 14 and 21 days and the amount of GAG accumulated within the matrix, the DNA content and the rate of $^{35}$S-sulfate incorporation were measured (FIG. 6). After 7 days in culture, the amount of GAG deposited in the matrix was unaffected by the addition of HA. However, the rate of sulfate incorporation was enhanced at 3 and 7 days by the addition of HA. After 14 days in culture, the rate of synthesis and the amount of accumulated GAG were both enhanced by adding exogenous HA. At 21 days, the effect on accumulation was not as great and there was no effect on sulfate incorporation. The DNA content was not affected significantly by the addition of HA except at 3 days when it was reduced.

These results suggest that the influence that HA bears on MSCs is more apparent when the cells already have initiated the process of differentiation, and that early events appear not to be influenced. This might suggest that HA influences the deposition and assembly of an integrated matrix, with a consequent feedback activation of proteoglycan synthesis.

EXAMPLE 4

Influence of Cell Density

Because chondrogenesis depends on contact between neighboring cells, it may be expected that cell density would have an effect on the rate at which matrix was deposited. The alginate layer system offers the ideal format for evaluating factors such as cell density because the cultures are prepared as a suspension of cells in liquid alginate. In this particular experiment, cells were seeded into alginate layers at densities ranging from 1.56 to $50 \times 10^6$ cells/ml. Each layer was cultured for 14 days under chondrogenic conditions and in the presence of TGF-β3. The rate of $^{35}$S-sulfate incorporation was determined by adding labeled sulfate 24 hours prior to harvesting (FIG. 7). The DNA content was also measured. Some clumping of cells was apparent at all cell densities. At cell seeding densities of less than $6.25 \times 10^6$ cells/ml, $^{35}$S-sulfate levels approached background after 14 days in culture (FIG. 7). However, a cell density of $6.25-25 \times 10^6$ cells/ml showed increasing levels of GAG synthesis. At a cell density of $50 \times 10^6$ cells/ml, there was little enhancement in biosynthesis compared to cultures at $25 \times 10_6$ cell/ml (FIG. 7).

EXAMPLE 5
Hyaluronan Exerts a Greater Effect at Lower Cell Density

Figure 8:
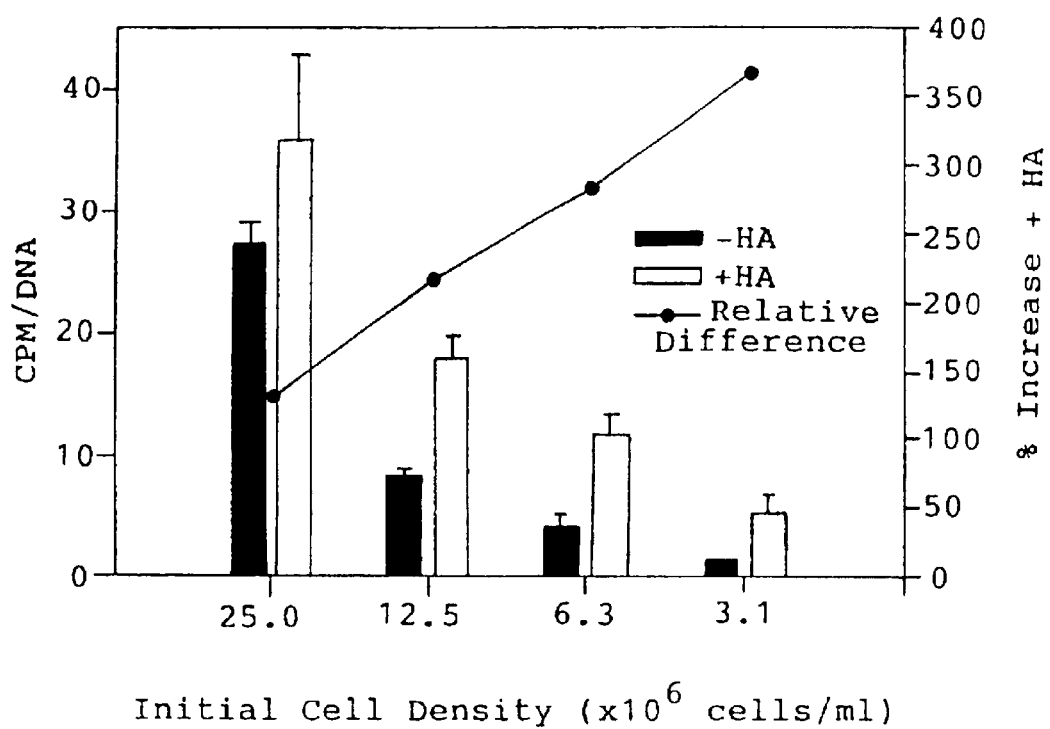
FIG. 8. Effect of HA on GAG synthesis at varying initial cell densities of MSCs.

A study was carried out to assess ho GAG synthesis was affected at different cell densities by HA addition. When cells were cultured in alginate at densities ranging from $3.2-25 \times 10^6$ cells/ml with and without HA (FIG. 8), it was evident that (1) HA had a positive effect on GAG synthesis at all densities and (2) the magnitude of the effect increased as the cell density decreased. This suggested that HA, at least in part, overcame the inhibition caused by low cell-cell contact. Other experiments (not shown) indicated that at higher cell density ($50 \times 10^6$ cells/ml) the addition of HA was without effect.

SUMMARY

These results indicate the following: (1) the rate of chondrogenic differentiation is enhanced when MSCs are cultured in alginate layers rather than pellets; (2) the rate of chondrogenesis is enhanced when HA is added at either 100 or 250 µg/ml to the culture medium; (3) the rate of chondrogenesis is enhanced when cultures in alginate are seeded with cells at a density $25 \times 10^6$ cells/ml, and reduced at lower densities; (4) the positive effect of added HA is evident at all cell densities up to $50 \times 10^6$ cells/ml and the magnitude of the effect increases as the cell density decreases.

What is claimed is:

1. A composition for producing cartilage, comprising human mesenchymal stem cells in an alginate gel layer which supports the differentiation and maturation of human mesenchymal stem cells into chondrocytes and hyaluronic acid, and wherein the mesenchymal stem cells in the gel layer have been contacted with a chondroinductive agent.

2. The composition of claim 1 wherein said chondroinductive agent is selected from the group consisting of a glucocorticoid and a member of the transforming growth factor superfamily.

3. The composition of claim 2 wherein said chondroinductive factor is TGF-β3.

4. The composition of claim 1 wherein said mesenchymal stem cells are in said alginate gel layer at a density from $3.2 \times 10^6$ cells/ml to $25 \times 10^6$ cells/ml.

5. The composition of claim 4 wherein said mesenchymal stem cells are in said alginate gel layer at a density from $6.25 \times 10^6$ cells/ml to $25 \times 10^6$ cells/ml.

6. A method for regenerating or repairing cartilage in an individual in need thereof comprising administering to said individual human a composition comprising mesenchymal stem cells in an alginate gel layer which supports the differentiation and maturation of human mesenchymal stem cells into a chondrogenic lineage to an extent sufficient to accelerate cartilage formation therefrom and hyaluronic acid, and wherein the mesenchymal stem cells in the gel layer have been contacted with a chondroinductive agent.

7. The method of claim 6 wherein said chondroinductive agent is selected from the group consisting of a glucocorticoid and a member of the transforming growth factor superfamily.

8. The method of claim 7 wherein said chondroinductive agent is TGF-β3.

9. The method of claim 6 wherein said mesenchymal stem cells are in said alginate gel layer at a density from $3.2 \times 10^6$ cells/ml to $25 \times 10^6$ cells/ml.

10. The method of claim 9 wherein said mesenchymal stem cells are in said alginate gel layer at a density from $6.25 \times 10^6$ cells/ml to $25 \times 10^6$ cells/ml.

11. A method of forming cartilage in vitro, comprising:

admixing human mesenchymal stem cells with a solution comprising an alginate and hyaluronic acid;

polymerizing said alginate to form a composition comprising said human mesenchymal stem cells in an alginate gel layer; and contacting said human mesenchymal stem cells in the alginate gel layer with a chondroinductive agent.

12. The method of claim 11 wherein said alginate is sodium alginate.

13. The method of claim 11 wherein said chondroinductive agent is selected from the group consisting of a glucocorticoid and a member of the transforming growth factor superfamily.

14. The method of claim 13 wherein said chondroinductive agent is TGF-β3.

15. The method of claim 11 wherein said mesenchymal stem cells are in said alginate gel layer at a density from $3.2 \times 10^6$ cells/ml to $25 \times 10^6$ cells/ml.

16. The method of claim 15 wherein said mesenchymal stem cells are in said alginate gel layer at a density of from $6.25 \times 10^6$ cells/ml to $25 \times 10^6$ cells/ml.

* * * * *